United States Patent [19]

Kummer et al.

[11] 4,338,926
[45] Jul. 13, 1982

[54] BONE FRACTURE PROSTHESIS WITH CONTROLLED STIFFNESS

[75] Inventors: Frederick J. Kummer, Hackensack, N.J.; Richard D. Coutts, San Diego, Calif.

[73] Assignee: Howmedica, Inc., New York, N.Y.

[21] Appl. No.: 208,906

[22] Filed: Nov. 21, 1980

[51] Int. Cl.³ .......................... A61F 5/04; A61B 17/18
[52] U.S. Cl. .......................... 128/92 BC; 128/92 BA; 128/92 C; 128/92 D; 3/1.9
[58] Field of Search ............ 128/92 B, 92 BA, 92 BB, 128/92 BC, 92 C, 92 D, 92 G; 3/1.9, 1.91

[56] References Cited

U.S. PATENT DOCUMENTS

| | | | |
|---|---|---|---|
| 2,136,471 | 11/1938 | Schneider | 128/92 BC |
| 2,987,062 | 6/1961 | Ellison | 128/92 B |
| 3,272,204 | 9/1966 | Artandi et al. | 128/334 R |
| 3,463,158 | 8/1969 | Schmitt et al. | 128/334 R |
| 3,596,656 | 8/1971 | Kaute | 128/92 D |
| 3,636,956 | 1/1972 | Schneider | 128/335.5 |
| 3,739,773 | 6/1973 | Schmitt et al. | 128/92 BC |
| 3,892,649 | 7/1975 | Phillips et al. | 128/92 C X |
| 3,918,100 | 11/1975 | Shaw et al. | 128/92 G X |
| 4,146,936 | 4/1979 | Aoyagi et al. | 128/92 C X |
| 4,186,448 | 2/1980 | Brekke | 3/1.9 |
| 4,192,021 | 3/1980 | Deibig et al. | 3/1.9 |
| 4,279,249 | 7/1981 | Vert et al. | 128/92 D |
| 4,280,233 | 7/1981 | Raab | 3/1.91 |
| 4,292,694 | 10/1981 | Koeneman | 3/1.91 |
| 4,292,695 | 10/1981 | Koeneman | 3/1.91 |

FOREIGN PATENT DOCUMENTS 1949923  4/1971  Fed. Rep. of Germany .... 128/92 B

OTHER PUBLICATIONS

"A Simple Method of Onlay Bone Grafting" by A. B. Young et al., The Lancet, Dec. 8, 1962, pp. 1186-1187.
Bradley, G. W. et al., "Effects of Flexural Rigidity of Plates on Bone Healing", Jour. Bone & Joint Surg., 61-A(6), pp. 866-872, (Sep. 1979).
Parsons, J. R. et al., "A Variable Stiffness, Absorbable Bone Plate", Trans Eleventh Int. Biomaterials Symp., Clemson, S. C., vol. III, p. 105 (1979).

Primary Examiner—Ronald L. Frinks
Attorney, Agent, or Firm—Francis X. Murphy; Charles J. Knuth; Lawrence C. Akers

[57] ABSTRACT

A novel bone prosthesis for use in healing a bone fracture is disclosed comprising a strong, rigid non-absorbable structural member and a biologically absorbable element held in use under compression against the structural member. Use of the novel prosthesis combines an excellent initial stabilization of the fixed fracture with a gradual shifting of stress-bearing from the prosthesis to the bone in the fracture region as the fracture heals. Thus, problems associated with stress-shielding during healing are alleviated. The structural member may be, e.g., a bone plate, intramedullary rod or hip nail.

9 Claims, 6 Drawing Figures

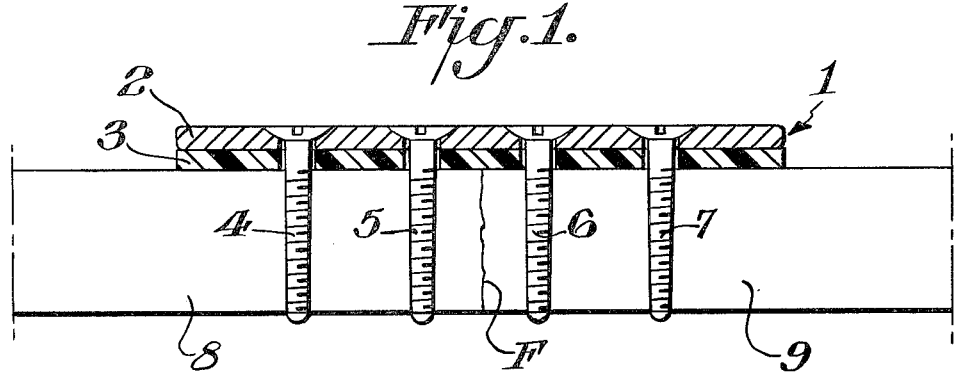
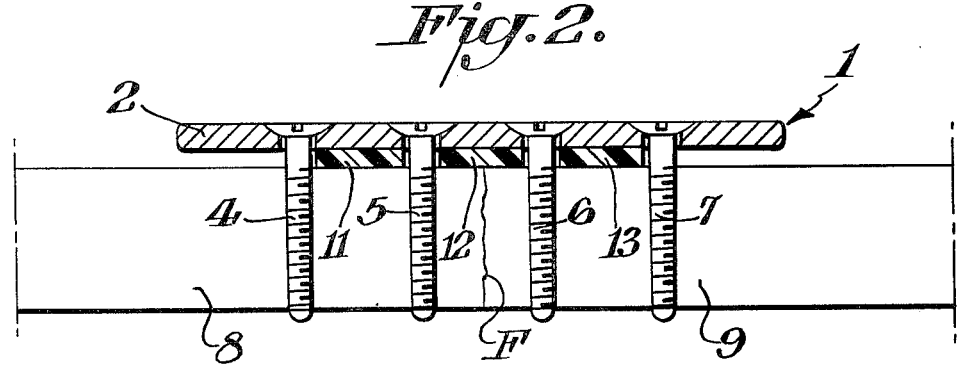
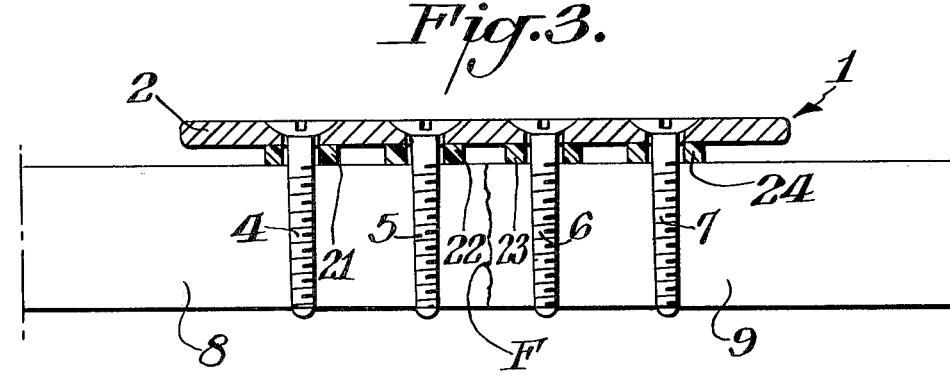

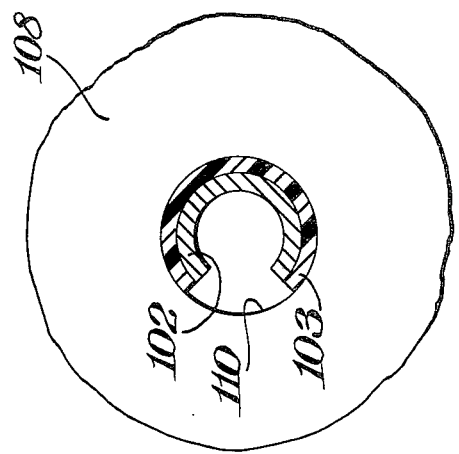
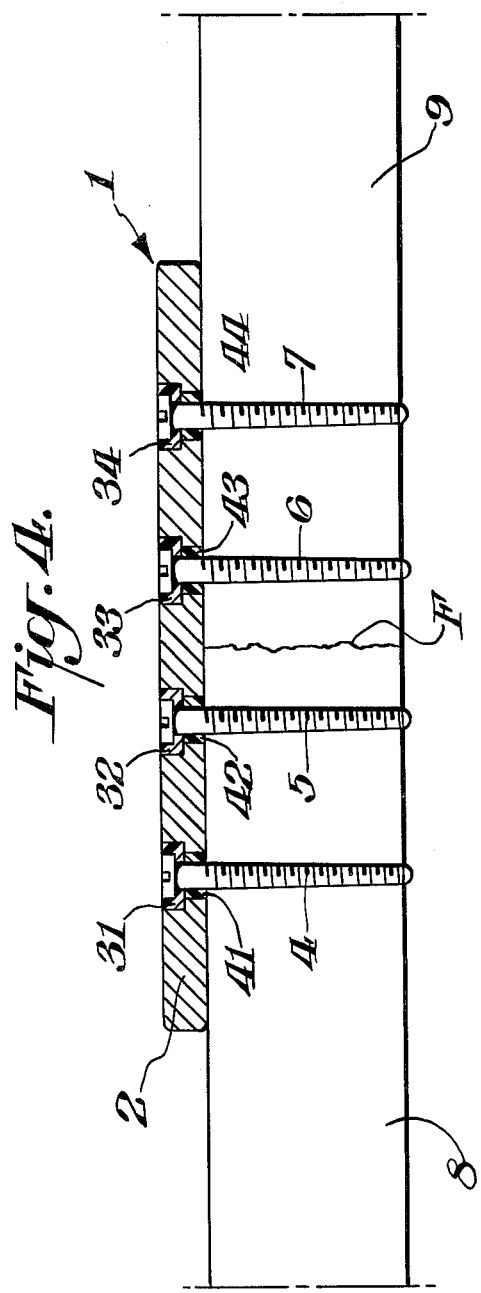
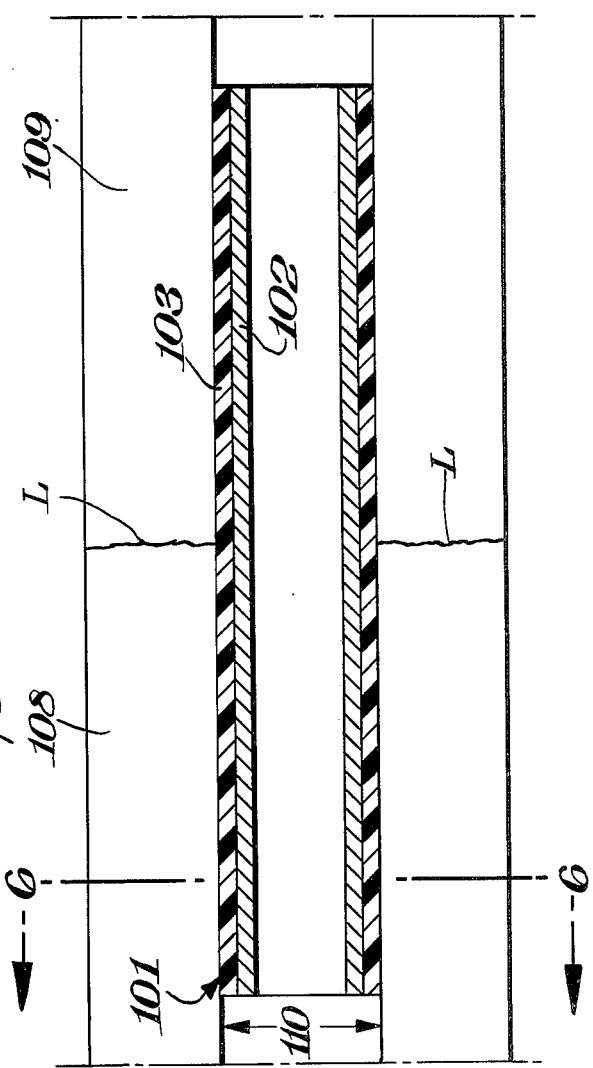

BONE FRACTURE PROSTHESIS WITH CONTROLLED STIFFNESS

BACKGROUND OF THE INVENTION

A wide variety of rigid metal prostheses, such as bone plates, intramedullary rods and femoral nails, are used in the fixation of bone fractures. A potential problem associated with the use of rigid bone prostheses for fracture fixation is referred to in the art as stress-shielding. As bone remodeling takes place in the region of the fracture, stresses exerted on the healing bone are carried primarily by the prosthesis rather than by the bone in the fracture region. This stress-shielding can be the cause of significant bone resorption, with consequent reduction of strength of the bone in the region of the healed fracture. Shielding of bending stresses from bone undergoing remodeling is believed to be particularly deleterious. See Bradley, G. W. et al., "Effects of Flexural Rigidity of Plates on Bone Healing", *Jour. Bone and Joint Surg.*, Vol. 61-A, No. 6, pp. 866-872 (September 1979) and Woo, S. L-Y et al., "A Comparison of Cortical Bone Atrophy Secondary to Fixation with Plates with Large Differences in Bending Stiffness", *Jour. Bone and Joint Surg.*, Vol. 58-A, No. 2, pp. 190-195 (March 1976).

The use of bone prostheses made of materials that are substantially less rigid than conventional surgical implant alloys has been proposed in order to alleviate problems arising from stress-shielding. One class of materials of reduced rigidity consists of non-absorbable synthetic polymers reinforced with inorganic fibers. However, the use of such materials sacrifices the excellent initial stabilization provided by a rigid prosthesis, which insures the maintenance of a proper alignment of bone segments during the early stages of healing.

U.S. Pat. No. 2,987,062 discloses an orthopedic bone fracture clamp adapted to be wrapped around a fractured bone. The clamp comprises two metallic bands directly connected at one pair of ends and joined by a link of absorbable catgut at the other pair of ends. The assembly of bands and absorbable link is placed under tension so as to hold the fractured bone together. After implantation of the assembly in the patient the link begins to be absorbed. Eventually the link fails and the clamping pressure on the bone is terminated, thereby, according to the patent, obviating the deleterious effects of continued pressure on the bone and eliminating the need for a second surgical operation to remove the clamp. However, the clamping pressure applied to the healing bone would not tend to decrease gradually or progressively with time after implantation. Instead, it would tend to drop in one full step at the moment of failure of the link from near the initial clamping pressure to zero.

The use of a bone plate having a rigidity that gradually decreases with time after implantation has been proposed by Parsons, J. R. et al., "A Variable Stiffness, Absorbable Bone Plate", presented at the Fifth Annual Meeting of the Society for Biomaterials, Clemson, South Carolina, April 28-May 1, 1979. The bone plate proposed by Parsons et al. is made of a material consisting of continuous carbon fibers embedded in a resorbable matrix of polylactic acid polymer. However, the initial rigidity of this plate is only 20% to 50% that of conventional stainless steel bone plates, and the rigidity decreases by only 10% after six weeks of implantation. Also, the carbon fibers are dispersed throughout the tissue of the patient after absorption of the polylactic acid matrix.

SUMMARY OF THE INVENTION

A novel bone prosthesis for use in healing a bone fracture has now been invented comprising a strong, rigid, biologically non-absorbable structural member and a biologically absorbable element adapted to be held under compression against said structural member when said prosthesis is secured to said bone, so that stress is transmitted from said bone through said element to said structural member, whereby the stress transmitted to said prosthesis gradually decreases with time during the healing of said bone as said element is absorbed. The structural member is preferably made of metal, but may also be made of a ceramic, carbonaceous or other material. The biologically absorbable element is preferably made of a synthetic polymeric material, such as a hydroxymethacrylate polymer, a polypeptide, polyglycolic acid, polylactic acid or a copolymer of polyglycolic acid and polylactic acid, but may also be made of, e.g., a ceramic material such as hydroxyapatite or tricalcium phosphate or a naturally-occurring polymeric material. The structural member of the novel prosthesis of the invention may be, e.g., a bone plate, intramedullary rod or hip nail. The effective overall rigidity of the prosthesis, as experienced by the healing bone, varies progressively with time after implantation, with stresses transmitted through the healing bone being gradually shifted from the prosthesis to the bone in the fracture region. The rate of decline of said effective rigidity as a function of time can be controlled by proper choice of the material (chemical composition, porosity, molecular weight, degree of crystallinity, monomeric ratio in copolymer, etc.) used for the biologically absorbable element.

A prosthesis of the invention may be designed in such a manner that its effective overall rigidity varies progressively after implantation from almost that of the rigid structural member to zero, with the probability of having to perform a subsequent surgical operation to remove the non-absorbable portion of the prosthesis being substantially lower than when said portion is implanted alone.

DETAILED DESCRIPTION OF THE INVENTION

The invention will be described in detail with reference to certain preferred embodiments thereof. Reference to these embodiments does not limit the scope of the invention, which is limited only by the scope of the claims.

In the drawings:

FIG. 1 is a front sectional view of a first embodiment of the invention, a bone plate provided with a continuous biologically absorbable coating;

FIG. 2 is a front sectional view of a second embodiment of the invention, a bone plate provided with a plurality of biologically absorbable spacers;

FIG. 3 is a front sectional view of a third embodiment of the invention, a bone plate provided with a plurality of biologically absorbable washers;

FIG. 4 is a front sectional view of a fourth embodiment of the invention, a bone plate provided with a plurality of biologically absorbable gaskets and non-absorbable sleeves;

FIG. 5 is a front sectional view of a fifth embodiment of the invention, an intramedullary rod provided with a continuous biologically absorbable coating; and FIG. 6 is sectional view taken along line 6—6 of FIG. 5.

FIG. 1 is a front sectional view of a first embodiment of the invention, bone prosthesis 1, secured to bone fragments 8 and 9 so as to effect the healing of a fracture between said bone fragments represented by fracture line F. Prosthesis 1 comprises a metallic structural member 2 and a biologically absorbable element 3. Structural member 2 is a conventional bone plate. Prosthesis 1 is secured to the bone by means of a plurality of conventional metallic bone screws 4 to 7 fitted through a plurality of circular apertures in member 2. Structural member 2 and bone screws 4 to 7 are made of a strong, rigid, biologically non-absorbable surgical implant alloy such as the cobalt-chromium-molybdenum alloy manufactured and sold under the trademark Vitallium (Howmedica, Inc.; New York, New York) or 316L stainless steel.

Element 3 is a biologically absorbable continuous coating molded to the bottom face of member 2 and having the same length and width as said face. Element 3 is typically from about 0.1 mm. to about 1 mm. in thickness. The absorbable coating is provided with a plurality of circular bone screw apertures coinciding with those in member 2. Element 3 is made of a synthetic polymeric material, preferably polyglycolic acid, polylactic acid or a polyglycolic acid:polylactic acid copolymer. As can be seen in FIG. 1, elements 3 is held under compression between structural member 2 and bone fragments 8 and 9 when prosthesis 1 is secured to said fragments by means of bone screws 4 to 7. The face of element 3 held adjacent to the bone fragments may be textured to allow for access of blood to the bone. Immediately after implantation, virtually all of the stresses transmitted between bone fragments 8 and 9 are transmitted through element 3 and carried by member 2, since they cannot be transmitted across the fracture line F. The rigidity of prosthesis 1 experienced by the bone fragments immediately after fixation is almost that of a conventional rigid metallic bone plate.

As time passes after implantation, two phenomena occur simultaneously. First, the fracture between fragments 8 and 9 begins to heal, thus reducing the need for stress-shielding. Second, element 3 is gradually absorbed by the bodily fluids and is thus gradually weakened. As these two phenomena occur, the pathway of stress transmission between bone fragments 8 and 9 is gradually shifted so that with passing time progressively more stress is transmitted directly through the healing bone in the region of original fracture line F and progressively less stress is transmitted through prosthesis 1. Finally, as the absorption of element 3 nears completion, virtually all of the stresses are carried by the healed bone itself; the probability of having to perform a subsequent surgical operation to remove the non-absorbable portion of the prosthesis is substantially lower than when said portion is implanted by itself without element 3.

Alternate designs for biologically absorbable elements for use with structural member 2 and screws 4 to 7 are shown in FIGS. 2, 3 and 4. In FIG. 2, the continuous coating 3 of FIG. 1 has been replaced by a plurality of discrete, generally rectangular biologically absorbable spacers 11 to 13 molded to the bottom face of structural member 2. The width of said spacers, i.e. the dimension extending perpendicularly to the plane of FIG. 2, is the same as the width of the bottom face of member 2. In FIG. 3, the continuous coating 3 of FIG. 1 has been replaced by a plurality of biologically absorbable washers 21 to 24 for screws 4 to 7. Washers 21 to 24 are not molded to structural member 2, and are separable therefrom when the prosthesis of FIG. 3 is not in use. In FIG. 4, the continuous coating 3 of FIG. 1 has been replaced by a plurality of biologically absorbable gaskets 31 to 34 for screws 4 to 7. Additionally, the prosthesis contains a plurality of non-absorbable polymeric, e.g. polyethylene, sleeves 41 to 44 located within the bone screw apertures of structural member 2 to prevent fretting of bone screws 4 to 7 against member 2. Gaskets 31 to 34 and sleeves 41 to 44 are separable from member 2 when the prosthesis of FIG. 4 is not in use.

FIG. 5 is a front sectional view of a fifth embodiment of the invention, bone prosthesis 101, which has been driven into the medullary canal 110 of a fractured bone so as to effect the healing of a fracture, represented by fracture line L, between bone fragments 108 and 109. Prosthesis 101 comprises a metallic structural member 102, which is a conventional intramedullary rod, and a biologically absorbable element 103, which is a continuous coating molded to the exterior surface of member 102. As can be seen in FIG. 6, both member 102 and element 103 are circular in transverse cross-section, subtending an angle of about 270°. Structural member 102 is made of a strong, rigid, biologically non-absorbable surgical implant alloy such as the cobalt-chromium-molybdenum alloy manufactured and sold under the trademark Vitallium (Howmedica, Inc.; New York, New York). Element 103 is made of a synthetic polymeric material, preferably polyglycolic acid, polylactic acid or a polyglycolic acid:polylactic acid copolymer. As can be seen in FIGS. 5 and 6, element 103 is held under compression between structural member 102 and bone fragments 108 and 109 when prosthesis 101 is driven into the medullary canal of the fractured bone. As bone healing and absorption of element 103 occur simultaneously after implantation, stress transmission is gradually shifted from prosthesis 101 to the bone in the region of original fracture line L in an analogous manner as described above with regard to the prostheses of FIGS. 1 to 4. Again, the probability of having to perform a subsequent surgical operation to remove structural member 102 is substantially reduced.

We claim:

1. A bone prosthesis for use in healing a bone fracture comprising a strong, rigid, biologically non-absorbable metallic structural member having a first surface adapted to face said bone on both sides of said fracture and a second surface facing substantially away from said first surface and separated therefrom by the thickness of said structural member, and a biologically absorbable, biodegradable synthetic polymeric element adapted to be held under compression between said structural member and said bone, with said element contacting at least a portion of said first surface but not contacting said second surface, when said prosthesis is secured to said bone, so that stress is transmitted from said bone through said element to said structural member, whereby the stress transmitted to said prosthesis gradually decreases with time during the healing of said bone as said element is absorbed.

2. A prosthesis of claim 1 wherein said structural member is an intramedullary rod and said element is affixed to the exterior of said rod.

3. A prosthesis of claim 1 wherein said structural member is a bone plate and said element is affixed to said plate.

4. A bone prosthesis for use in healing a bone fracture comprising a strong, rigid, biologically non-absorbable structural member, distinct means to secure said structural member to said bone, and a biologically absorbable element adapted to be held under compression between said securing means and said structural member when said prosthesis is secured to said bone, so that stress is transmitted from said bone through said element to said structural member, whereby the stress transmitted to said prosthesis gradually decreases with time during the healing of said bone as said element is absorbed.

5. A prosthesis of claim 4 wherein said structural member is a bone plate, said securing means comprises a bone screw adapted to be fitted through an aperture in said plate, and said element is a gasket held between said screw and said plate.

6. A bone prosthesis for use in healing a bone fracture comprising a strong, rigid, biologically non-absorbable structural member and a biologically absorbable element adapted to be held under compression between said structural member and said bone when said prosthesis is secured to said bone, so that stress is transmitted from said bone through said element to said structural member, with said structural member being a bone plate adapted to be secured to said bone by means including a bone screw adapted to be fitted through an aperture in said plate, and with said element being a washer for said screw held between said plate and said bone, whereby the stress transmitted to said prosthesis gradually decreases with time during the healing of said bone as said element is absorbed.

7. A prosthesis of claim 4 or 6 wherein said element is made of a polymeric material.

8. A prosthesis of claim 4 or 6 wherein said element is made of a synthetic polymeric material.

9. A bone prosthesis for use in healing a bone fracture comprising a strong, rigid, biologically non-absorbable metallic structural member and a biologically absorbable, biodegradable synthetic polymeric element adapted to be held under compression between said structural member and said bone when said prosthesis is secured to said bone, so that stress is transmitted from said bone through said element to said structural member, with said structural member being a bone plate adapted to be secured to said bone by means comprising two bone screws each adapted to be fitted through an aperture in said plate, and with said element being a spacer held between said plate, said bone and said two screws, whereby the stress transmitted to said prosthesis gradually decreases with time during the healing of said bone as said element is absorbed.

* * * * *